(12) United States Patent
Greene et al.

(10) Patent No.: US 6,695,814 B2
(45) Date of Patent: *Feb. 24, 2004

(54) SAFETY INTRAVENOUS CATHETER ASSEMBLY AND METHOD FOR USE WITH A NEEDLE

(75) Inventors: Elliott Stephen Greene, Altamont, NY (US); Jason Andrew Greene, Lancaster, PA (US)

(73) Assignee: Albany Medical College, Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 84 days.

This patent is subject to a terminal disclaimer.

(21) Appl. No.: 09/840,699

(22) Filed: Apr. 23, 2001

(65) Prior Publication Data

US 2001/0014786 A1 Aug. 16, 2001

Related U.S. Application Data

(63) Continuation of application No. 09/127,374, filed on Jul. 31, 1998, now Pat. No. 6,221,047.

(51) Int. Cl.[7] ............................................. A61M 5/178
(52) U.S. Cl. .................. 604/164.08; 604/198; 604/263
(58) Field of Search .................. 604/93, 162, 164, 604/167, 171, 192, 198, 263, 195, 197, 164.01, 93.01, 164.07, 164.08, 164.11, 165.01, 165.02, 167.01, 167.06

(56) References Cited

U.S. PATENT DOCUMENTS

| 4,944,725 | A | * | 7/1990 | McDonald | 604/164 |
|---|---|---|---|---|---|
| 4,952,207 | A | | 8/1990 | Lemieux | 604/164 |
| 4,964,854 | A | | 10/1990 | Luther | 604/166 |
| 4,978,344 | A | | 12/1990 | Dombrowski et al. | 604/198 |
| 5,135,504 | A | | 8/1992 | McLees | 604/164 |
| 5,215,525 | A | | 6/1993 | Sturman | 604/164 |
| 5,300,045 | A | | 4/1994 | Plassche, Jr. | 604/263 |
| 5,366,447 | A | | 11/1994 | Gurley | 604/192 |
| 5,419,766 | A | | 5/1995 | Chang et al. | 604/110 |
| 5,458,658 | A | * | 10/1995 | Sircom | 604/192 |
| 5,549,558 | A | | 8/1996 | Martin | 604/110 |
| 5,558,651 | A | | 9/1996 | Crawford et al. | 604/263 |
| 5,599,310 | A | | 2/1997 | Bogert | 604/164 |
| 5,688,249 | A | | 11/1997 | Chang et al. | 604/198 |
| 5,700,250 | A | | 12/1997 | Erskine | 604/263 |
| 5,910,132 | A | | 6/1999 | Schultz | 604/162 |
| 5,935,109 | A | | 8/1999 | Donnan | 604/164 |
| 5,935,110 | A | | 8/1999 | Brimhall | 604/167 |
| 5,951,515 | A | * | 9/1999 | Osterlind | 604/110 |
| 6,117,108 | A | | 9/2000 | Woehr et al. | 604/110 |
| 6,221,047 | B1 | * | 4/2001 | Greene et al. | 604/164 |

OTHER PUBLICATIONS

Greene, pending U.S. patent application, Ser. No. 10/120,005, filed Apr. 10, 2002, entitled "Safety Intravenous Catheter Assembly" (Attorney Docket No. 0410.006B).

* cited by examiner

Primary Examiner—Michael J. Hayes
Assistant Examiner—Jennifer Maynard
(74) Attorney, Agent, or Firm—Heslin Rothenberg Farley & Mesiti P.C.

(57) ABSTRACT

A safety intravenous catheter assembly and method for use with a needle in one embodiment includes a catheter hub and a needle cover attachable to and releasably lockable with the catheter hub when the needle extends through the needle cover. A stop assembly is attached to the needle and to the needle cover for maintaining a tip of the needle within the needle cover. The stop assembly includes a first irreversible locking position whereby the catheter hub cannot disengage from the needle cover, and a second locking position whereby the catheter hub can disengage from the needle cover.

22 Claims, 5 Drawing Sheets fig. 1 fig. 14 fig. 2   fig. 3   fig. 4

SAFETY INTRAVENOUS CATHETER ASSEMBLY AND METHOD FOR USE WITH A NEEDLE

RELATED APPLICATION

This application is a continuation of U.S. patent application Ser. No. 09/127,374, filed Jul. 31, 1998 which issued as U.S. Pat. No. 6,221,047 on Apr. 24, 2001, the entirety of which is incorporated herein by reference.

TECHNICAL FIELD

This invention relates generally to catheter devices. More particularly, the invention relates to safety catheter devices having needlestick protection features and preferably automatic such features.

BACKGROUND ART

Intravenous (IV) catheters are medical devices used to obtain continuous vascular access in patients. Such a device generally consists of a hollow-bore needle stylet and an over-the-needle plastic type material catheter used to access the lumen of a blood vessel in a patient. The IV catheter is advanced into the vessel and is used for administering intravenous fluids, medications or blood products. Since the IV catheter is placed percutaneously, the hollow-bore needle stylet becomes blood contaminated and, when the blood vessel lumen is accessed, the needle-stylet becomes blood-filled.

Needlestick injuries from IV catheter stylets are in the high-risk category for potential transmission of bloodborne pathogens to the injured health care worker, since they are hollow-bore needles which are usually filled with undiluted blood. The bloodborne pathogens of greatest concern include human immunodeficiency virus (HIV), the etiologic agent of the acquired immunodeficiency syndrome (AIDS), hepatitis B virus and hepatitis C virus.

It is estimated at least 800,000 needlestick injuries from all types of needle devices occur in hospital settings each year in the United States. While nationwide data from 1995 indicate 7.3% of percutaneous injuries were from IV catheter stylets, the injury frequency is not the direct determinant of risk for infection transmission ("*Prevention, Management & Chemoprophylaxis of Occupational Exposure to HIV*" Advances in Exposure Prevention 1997; pp. 14–25). The type of device responsible for a percutaneous injury is a critical determinant of the potential for infection transmission. When the source patient is infected, devices which introduce a larger volume of blood inoculum into the injured health care worker are more likely to transmit infection. (Cardo D M, et al. *A case-control study of HIV seroconversion in health care workers after percutaneous exposure.* N Engl J Med 1997; 337: 1485–90). Injuries from hollow-bore blood-filled needles introduce a greater volume of blood inoculum into the injured health care worker than either non-blood-filled needles or solid-core needles. Twenty-five percent (25%) of percutaneous injuries from the above 1995 nationwide data were in the high-risk (blood-filled hollow-bore needle) category, and approximately 25% of the high-risk injuries were related to IV catheter insertion. An analysis of all devices causing percutaneous injuries indicated that IV catheter stylets were the number one cause of high-risk needlestick injuries (*Injuries from vascular devices: High risk and preventable.* Advances in Exposure Prevention 1998; 3:37–47). A study of health care workers with documented occupationally acquired HIV infections after percutaneous exposure to HIV-infected blood indicated 91% of seroconversions were from hollow-bore needle injuries and a high-risk factor for HIV seroconversion was a needle previously in a patient's vein or artery (a blood-filled needle) (Cardo D M, et al. N Engl J Med 1997; 337: 1485–90). These data indicate safety IV catheters are a high priority for safety devices in the health care setting.

An analysis of injuries from the 1995 nationwide data above indicates most would have been potentially preventable with use of safety devices (*Prevention, Management & Chemoprophylaxis of Occupational Exposure to HIV.* Advances in Exposure Prevention 1997; pp. 50–51). The Occupational Safety and Health Administration (OSHA) Bloodborne Pathogen Standard requires that engineering controls, including safety devices, be used along with other methods to reduce occupational exposure to bloodborne pathogens.

The Centers for Disease Control and Prevention (CDC) recommends "that safety devices include safety features that activate automatically and do not rely on activation by health care workers" (*CDC Morbidity and Mortality Weekly Report (MMWR)* Jan. 17, 1997, pp. 21–25). This preferred type of safety feature is passive, such that no activation by the user is necessary ("active" safety features require activation by the user, which depends on user compliance, and are therefore less desirable). An analysis of nationwide data support the recommendation for passive safety features: over 50% of injuries from safety IV catheter stylets occurred after placement of the IV catheter (i.e., after use of the stylet, or during or after disposal of the stylet) and most of these injuries occurred because the user did not place the stylet into its locked safety position (Advances in Exposure Prevention 1998; 3:37–47).

As of June 1998, only two types of safety IV catheters are marketed worldwide; however, neither adequately meets the CDC requirements. Disadvantages of both catheters include: activation of the safety feature depends on the health care worker's compliance with a specific IV catheter insertion/activation technique, and the safety feature can be bypassed if the catheter is used incorrectly, resulting in an unprotected contaminated needle tip. Of further significance, the insertion/activation techniques required for these catheters add additional steps and/or complexity to the IV catheter insertion process compared to standard non-safety IV catheters.

The need for improvement in IV catheters is apparent. The safety catheter of the present invention advantageously meets the CDC recommendation "that safety devices include safety features that activate automatically and do not rely on activation by health care workers." In addition, the insertion/activation technique required for the present invention advantageously does not add steps and/or complexity to the process of IV catheter insertion.

SUMMARY OF THE INVENTION

The shortcomings of the prior art are overcome and additional advantages are provided through the provision of a safety intravenous catheter assembly for use with a needle. The assembly preferably comprises the following. A catheter hub has an axial bore extending through the catheter hub. A needle cover has a first end of the needle cover insertable in the axial bore and a second axial bore extending through the needle cover and co-axial with the axial bore. A notch extends outwardly in the axial bore of the catheter hub. A notch clip is joined with the needle cover and is positionable to engage the notch of the catheter hub. The notch clip can engage a side of the needle and the notch and lock the catheter hub in engagement with the needle cover when the needle cover is inserted in the axial bore and the needle is inserted in the second axial bore at least adjacent or past a distal portion of the notch clip. Finally, the notch clip disengages the notch and enables the catheter hub to pass out of engagement with the needle cover when the needle is located in the second axial bore prior to the distal portion of the notch clip.

Another feature of the invention relates to a method for using a safety intravenous catheter assembly in combination with a needle. Preferably the method comprises: withdrawing the needle from a second axial bore, the second axial bore being located in a needle cover, and the needle cover including a notch clip positionable in engagement with an outwardly extending notch in a catheter hub; sliding the needle in engagement with the notch clip when withdrawing the needle from the second axial bore; forcing the notch clip into the second axial bore; and, disengaging the catheter hub from the needle cover.

Still another feature of the invention concerns practicing the method where, additionally or alternatively, the needle cover is inserted into the catheter hub and the catheter hub is locked in engagement with the needle cover wherein the locking relationship comprises engaging a side of the needle against the notch clip and maintaining the notch clip in the notch.

According to other features of the invention, there are provided automatic and/or continuous means for positioning the notch clip, particular notch and notch clip configurations, and a stop assembly to limit withdrawing of the needle from the needle cover.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be apparent from the following detailed description taken in conjunction with the accompanying drawings, which drawings illustrate several embodiments of the invention.

BEST MODE FOR CARRYING OUT THE INVENTION

Referring now to the drawings, and in particular FIGS. 1–4 for example, there is shown an embodiment of a safety intravenous catheter assembly 10 for use with a needle 12. Although not shown with the needle's open beveled end configuration facing the stop bar 42, this is the preferred orientation in practice. In addition, although not shown with the notch clip facing the opposite side of the needle's open beveled end (the longest part of the needle bevel), this is the preferred orientation in practice. The assembly includes a catheter cannula 19 and the attached catheter hub 18 having an axial bore 20 extending through the catheter hub. The assembly also includes a needle cover 22 having a first end 24 of the needle cover insertable in the axial bore. A second axial bore 26 extends through the needle cover 22 and is preferably co-axial with the axial bore 20 when in an assembled state. Except as specifically noted hereinafter, the components of the assembly are constructed out of materials similar to those for pre-existing IV catheters and related parts. For example, sterile grade rigid plastic can be used to form the catheter hub 18, needle cover 22, stop bar 42 and needle case 44. The stop bar 42 could alternatively be sterile grade stainless steel. The needle 12 may comprise a sterile grade stainless steel.

The assembly 10 further includes a notch 28 extending outwardly in the axial bore of the catheter hub. The notch is preferably a continuous circumferential notch. This enables the catheter hub to be rotated around the needle cover when the two are fully engaged, as desired.

Figure 1:
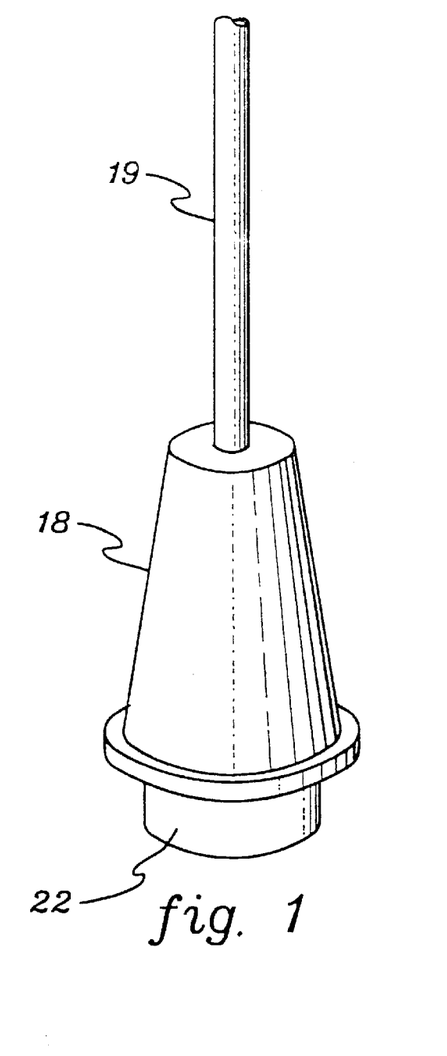
FIG. 1 is a perspective view of a catheter hub and needle cover without a stop member for an embodiment of a safety intravenous catheter assembly in accordance with the features of the invention.
Figure 2:
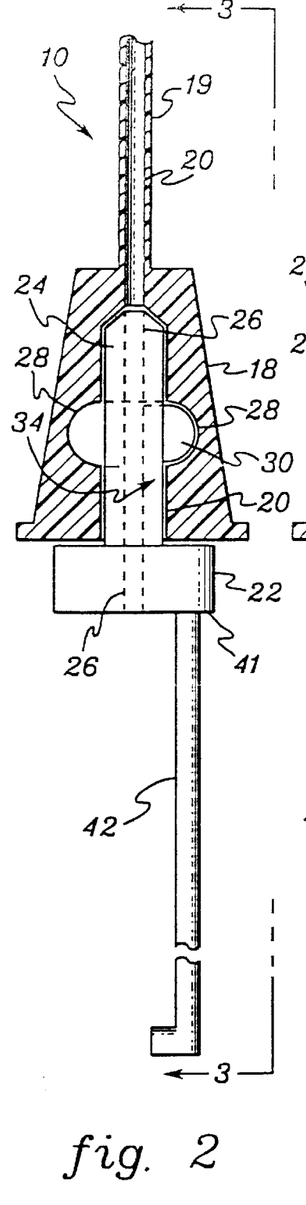
FIG. 2 is a cross-sectional side view of the catheter hub of FIG. 1 in combination with a side view of a needle cover fully inserted therein and a stop bar joined with the needle cover, in accordance with the features of the invention.
Figure 3:
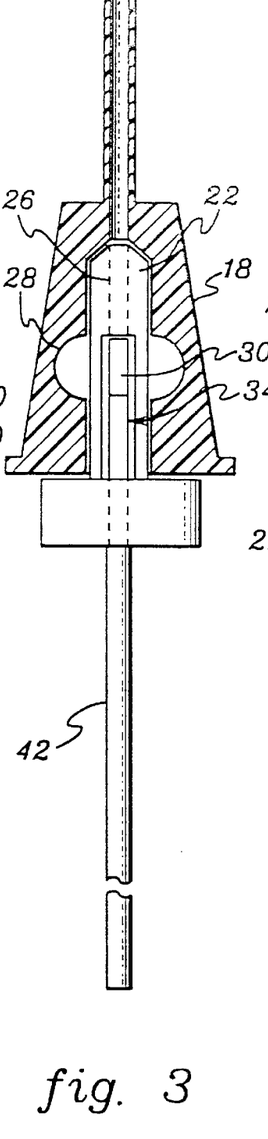
FIG. 3 is another view of the assembly of FIG. 2 taken along the line 3—3.
Figure 4:
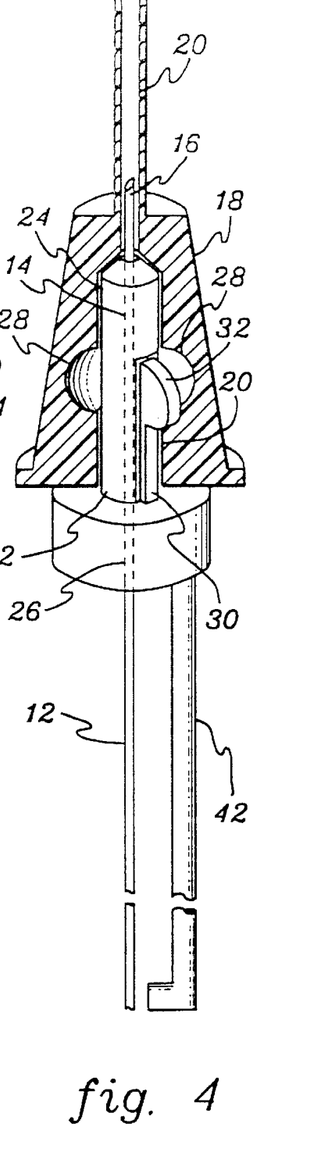
FIG. 4 is a partial perspective and cross-sectional side view of the assembly of FIG. 2 but with the needle cover rotated slightly and in combination with a needle inserted in the needle cover.
Figures 5, 6:
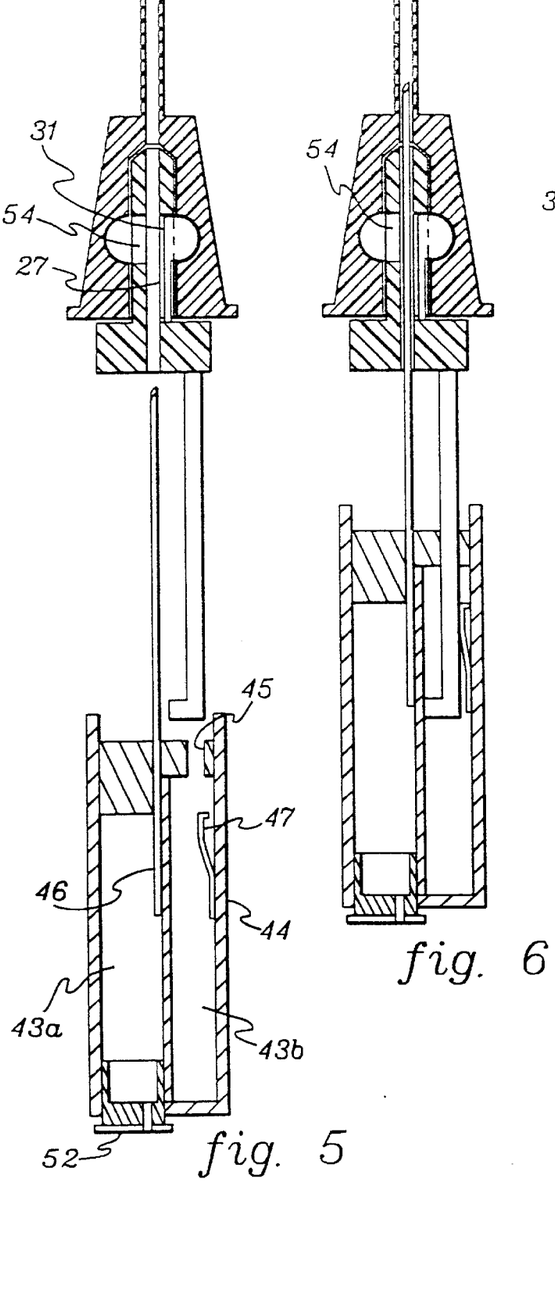
FIG. 5 is a cross-sectional side view of the assembly of FIG. 2 in combination with a needle and a needle case and just prior to insertion of the needle into the needle cover and the stop bar into the needle case.
FIG. 6 is a cross-sectional side view of the assembly of FIG. 2 in combination with a needle and a needle case and during insertion of the needle into the needle cover and the stop bar into the needle case.

The assembly still further includes a notch clip 30 joined with the needle cover and positionable to engage the notch 28 of the catheter hub. Preferably, the inner surface of the notch clip is substantially parallel to the second axial bore when in the rest position and not in forceful contact with the needle 12, so that the notch clip at most rests against the needle as in side-by-side non-forceful contact. More preferably, there is an annular space 31 (FIG. 5) adjacent the notch clip 30 with the space 31 located between the notch clip 30 and the second axial bore 26. In these preferred ways, the assembly can provide no frictional drag between the notch clip 30 and the needle 12 when the needle is inserted into and withdrawn from the needle cover. The notch clip and the needle cover could be formed integral. Alternatively, the notch clip could be an independent piece configured for a snap fit or bonded or glued relationship with the needle cover 22. Preferably the radially inward side or inner surface of the notch clip is in or adjacent the annular space and at most co-planar with a second surface 27 (FIG. 5) defined by an outer circumference of the second axial bore when the notch clip is at rest.

Figures 8, 9, 10:
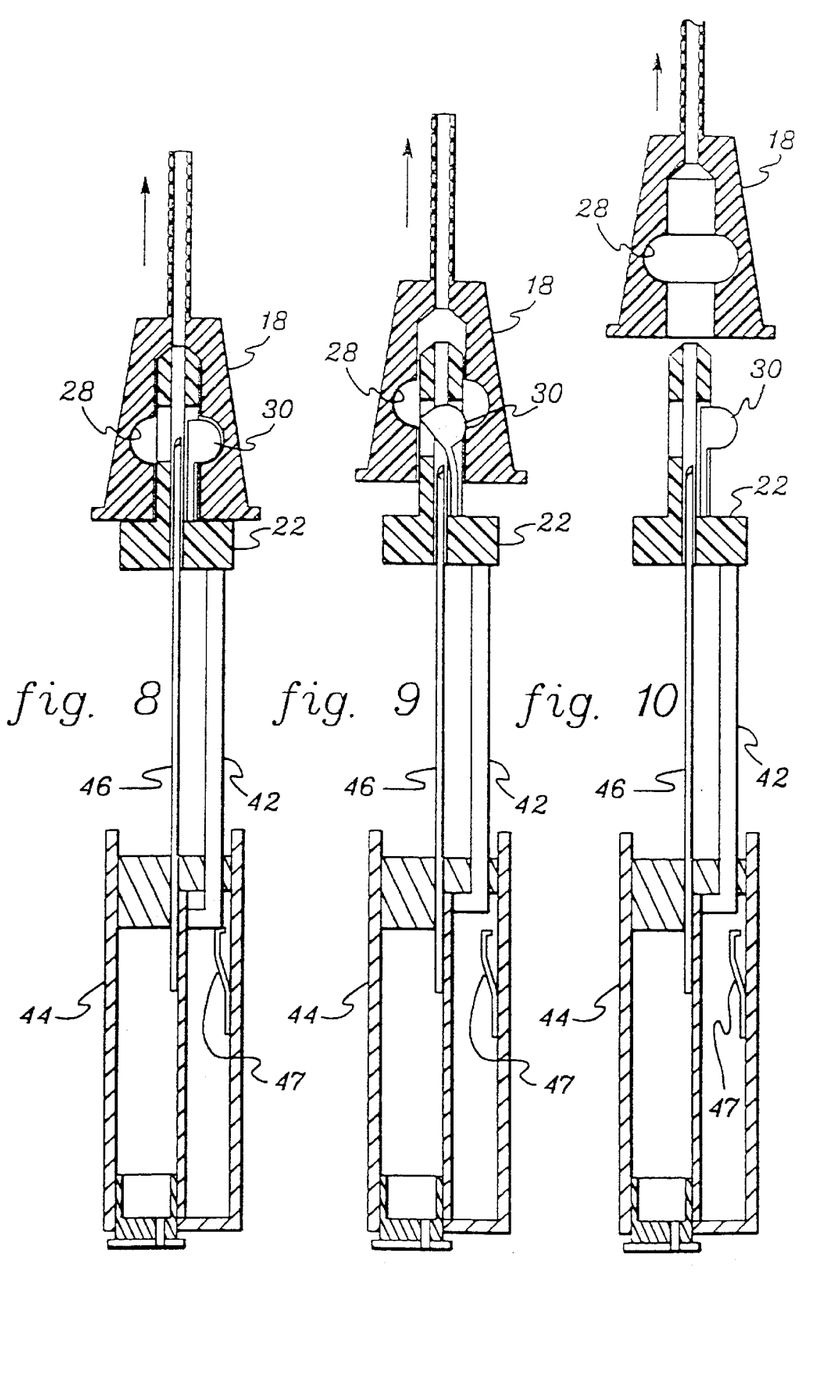
FIG. 8 is a cross-sectional side view of the assembly of FIG. 2 in combination with a needle and a needle case and with the needle being withdrawn from the distal end of the needle cover, with the needle tip adjacent to the distal portion of the notch clip, and with the stop bar locked into the needle case by detent 47.
FIG. 9 is a cross-sectional side view of the assembly of FIG. 2 in combination with a needle and needle case and with the needle being withdrawn from the distal portion of the notch clip, with the stop bar's L-shaped end abutting the end of the needle case, and with the catheter hub disengaging from the needle cover as the notch clip flexes inward.
FIG. 10 is a cross-sectional side view of the assembly of FIG. 2 in combination with a needle and a needle case and with the catheter hub being fully disengaged from the needle cover and with the stop bar in a stopped position within the needle case and thereby maintaining a tip of the needle within the needle cover.

The notch clip is preferably made of a resilient type material having a characteristic which enables it to flex radially inward with minimal force. This force is provided by notch 28 and a bottom portion of the catheter hub 18 as the hub disengages from the needle cover. This disengagement preferably only occurs when the needle tip 16 is located prior to the distal portion 32 of the notch clip (FIG. 9).

A relationship between the notch and the notch clip contributes to several of the features and advantages of the invention, as shown in the drawings FIGS. 5–10 for example, and explained herein. For example, when the needle cover is inserted in the axial bore and the needle is inserted in the second axial bore at least adjacent or past a distal portion 32 of the notch clip (FIGS. 6–8), the notch clip can engage a side 14 (FIG. 4) of the needle and the notch 28 and lock the catheter hub in engagement with the needle cover. The needle cover's and notch clip's preferred designs enable selective sliding engagement with side 14 of the needle and the inside of catheter hub 18 such that there is minimal, and preferably no, frictional drag so that catheter hub 18 can easily rotate around the needle axis, and also, so that the catheter hub and needle cover combined can easily move distally towards the needle tip 16 during IV catheter insertion. The distal portion 32 of the notch clip is preferably smoothly contoured to minimize frictional drag inside notch 28 during rotation.

For the notch clip design in the figures, as the safety intravenous catheter assembly 10 is assembled, the distal portion 32 of the notch clip naturally slips into notch 28 when the needle cover is loaded into catheter hub 18. This moves the notch clip distal portion 32 completely out of the second axial bore which permits preferred unrestricted movement of needle 12 into the second axial bore, thus facilitating easy assembly of the device.

Embodiments of the invention may include additional safety features such as a stop assembly joined with the needle cover at a second end 41 (FIGS. 2–14). The joined relationship may be obtained by forming integral or a conventional bonding or gluing process, or a snap-fit relation. The stop assembly serves to limit withdrawal of the needle from the needle cover by maintaining a tip 16 of the needle inside the second axial bore 26.

For example, in one embodiment, the stop assembly may comprise a stop bar 42 joined with the needle cover at the second end. In this embodiment the stop assembly further includes a needle case 44 joined with the needle at a first end 46 of the needle, such as by a conventional forming, bonding or gluing process. As should be apparent, the first end of the needle is in fluid flow communication with the needle case via a chamber 43a. The stop bar communicates with the needle case via an opening 45 in a second chamber 43b. The stop bar 42, needle case 44 and detent 47 are designed so that sliding movement of the stop bar has minimal frictional drag (FIGS. 5–10, 12–14). The stop bar and detent 47 may be of any design to stop the bar at the desired length of extension. The stop bar may also be designed to extend telescopically and then lock, which would decrease the needle case length.

The operation of the invention is shown in FIGS. 5–10. For assembly of the invention (FIGS. 5–7), the stop bar 42 of the assembly 10 is inserted into the needle case 44 and the needle 12 is aligned with the second axial bore 26. Any of several approaches could be used for assembly such as where the needle case is intact and fully enclosed or by having a side opening which is later covered and sealed closed. If the needle case is fully enclosed in final form and, for example, opening 45 is slot shaped, the stop bar can be rotated ninety degrees and inserted into the needle case and rotated back ninety degrees. The stop bar then passes by a resilient detent 47, by having detent 47 retracted radially outward to permit the stop bar to be inserted. For example, this radial retraction can be accomplished via a hook externally or other device via a small opening in the outside wall of chamber 43b or other conventional means.

Figure 7:
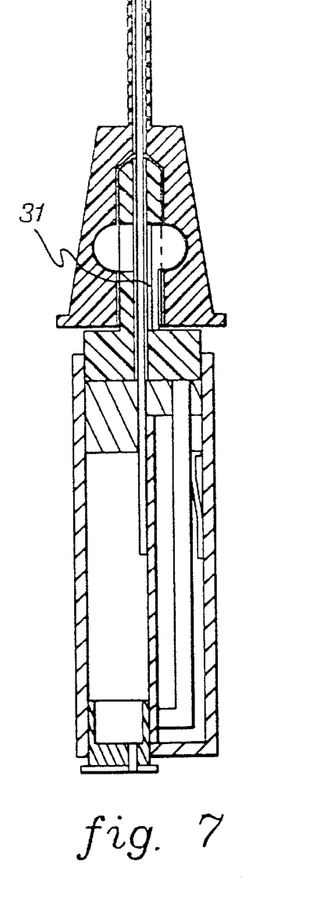
FIG. 7 is a cross-sectional side view of the assembly of FIG. 2 in combination with a needle and a needle case and with the needle fully inserted into the needle cover and the stop bar fully inserted into the needle case.

The process of catheter insertion (FIGS. 7–10) typically involves placing needle tip 16 into a vessel lumen, maintaining needle 12 stationary, advancing catheter cannula 19 into the vessel lumen until catheter hub 18 abuts the skin, and then completely withdrawing needle 12 from catheter hub 18. After placing needle tip 16 into the vessel lumen (FIG. 7) the user holds needle case 44 stationary (which maintains needle 12 stationary) and advances catheter cannula 19 into the vessel lumen until catheter hub 18 abuts the skin, and then needle case 44 is withdrawn to withdraw needle 12 from the catheter cannula 19 and partially withdraw needle 12 from catheter hub 18 (FIGS. 7–8). As stop bar 42 is withdrawn from the needle case (FIGS. 7–8), the detent 47 continues to be forced to the right until eventually, the L-shaped portion of the stop bar passes beyond the distal aspect of detent 47 and the detent can spring underneath the L-shaped portion (FIG. 8). This action serves to stop the re-insertion of the stop bar into the second chamber 43b. At this position the needle tip 16 is adjacent to the distal end 32 of the notch clip (FIG. 8). As the needle case and needle are further withdrawn, the stop bar is withdrawn a small amount more from the needle case, and now the needle tip is located prior to distal end 32 of the notch clip, which allows the catheter hub to be disengaged from the needle cover (FIG. 9). This preferred small additional movement of the stop bar ensures that the catheter hub does not disengage from the needle cover until the stop bar's L-shaped end is locked above detent 47 and the needle tip 16 is thereby locked inside the needle cover. Any alternative mechanism to detent 47 can be used as long as it functions to lock into the final position, as described above, the L-shaped or other shaped end of the stop bar and such that there is preferably a minimum of frictional drag during catheter insertion. Then, the catheter hub 18 can be fully disengaged from the needle cover 22 (FIG. 10).

In another embodiment (FIG. 11), the stop member may comprise a ring-like stop 48 joined with the needle cover 22 at the second end 41 and the needle 12 having a stop notch 50 located in the side of the needle. This embodiment is similar in all respects to the embodiment discussed previously, except as noted hereafter. In operation, as the needle is withdrawn from the needle cover, the ring-like stop engages the stop notch thereby maintaining needle tip 16 inside the second axial bore 26. Then the catheter hub 18 can be removed in a similar fashion as described previously. In this embodiment, the ring-like stop 48 is preferably constructed of a resilient material that is sized to automatically and continuously engage the circumference of the needle 12. When being assembled, the ring-like stop can be temporarily relaxed to enable insertion of the needle into the needle cover 22 and passing the stop notch 50 past the ring-like stop 48.

Figures 11, 12, 13:
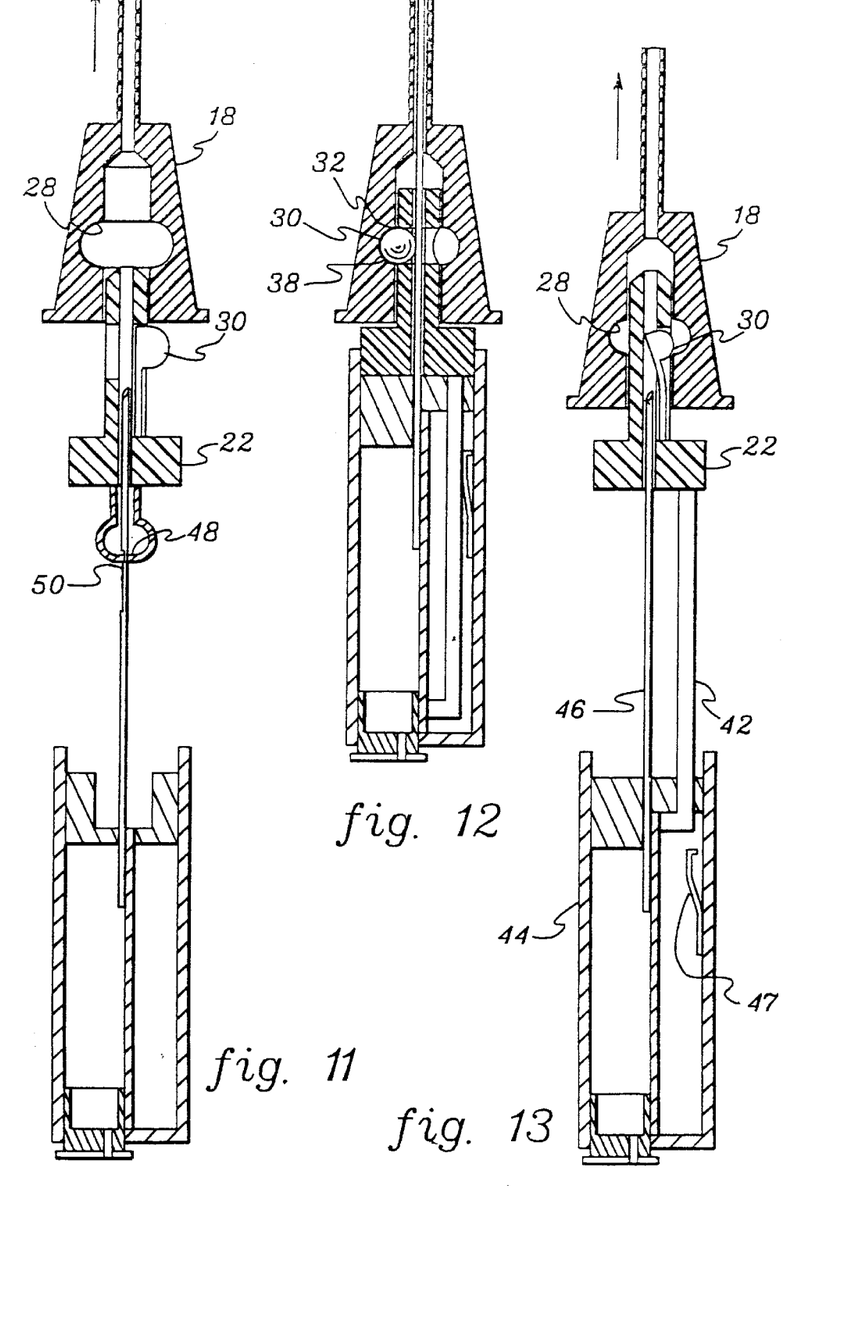
FIG. 11 is a cross-sectional side view of another embodiment of a safety intravenous catheter assembly in accordance with the features of the invention, here showing a ring-like stop of the needle cover engaging a stop notch of the needle for limiting withdrawal of the needle from the needle cover and where the catheter hub is being disengaged from the needle cover.
FIG. 12 is a cross-sectional side view of another embodiment of a safety intravenous catheter assembly in accordance with the features of the invention, but here showing a ball bearing type of notch clip and in combination with a needle and a needle case and with the needle fully inserted into the needle cover and the stop bar fully inserted into the needle case.
FIG. 13 is a cross-sectional side view of yet another embodiment of a safety intravenous catheter assembly in accordance with the features of the invention and similar in all respects to the assembly of FIG. 2, except here eliminating the notch 54 in the needle cover.

Other aspects of the invention may concern the notch clip comprising a member from the group consisting of a "p"-shaped finger 34 (e.g., FIGS. 2–11 and 13–14) or a ball bearing 38 (e.g., FIG. 12). The notch clip of each of these particular configurations operates similarly to that previously described herein.

Still other aspects of the invention concern a method for using the assembly 10 (FIGS. 5–10). For example, the assembly may be used as follows, where the steps can be arranged in various orders but are listed here in a preferred order. A first step includes inserting the needle cover 22 into the catheter hub 18 and locking the catheter hub in engagement with the needle cover. The step of locking comprises establishing and/or maintaining the notch clip in engagement with the notch (e.g., preferably by the notch clip having a resilient characteristic whereby its rest position creates an annular space 31 between itself and the second axial bore 26). The stop bar is simultaneously advanced into the needle case 44 (as described previously) until the needle cover 22 engages fully with the top of the needle case 44.

A next step is to insert the needle tip 16 and a portion of cannula 19 of the catheter into a recipient (e.g., the recipient's vein, etc.) which is indicated by a characteristic tactile sensation to the user inserting the cannula and blood appearing in chamber 43a. Next the cannula 19, typically, is completely advanced into the blood vessel while the needle case remains stationary. At this time the catheter hub 18 abuts the skin at the catheter insertion site. Then, since the needle cover 22 is still engaged in the catheter hub 18, the needle is withdrawn from the axial bore 20 and second axial bore 26. The needle withdraws relative to cannula portion 19 as the needle tip 16 slides towards the notch clip 30.

As the needle is withdrawn, it may selectively slide in engagement with the notch clip, thereby maintaining the distal portion of the notch clip in the notch and automatically preventing the hub from disengaging from the needle cover prematurely. Stated analogously, preferably the non-forceful contact relationship or annular space 31 is maintained between the notch clip 30 and the needle 12, so as to provide minimal, and preferably no, friction between the needle and the notch clip. However, any attempt to withdraw the needle cover 22 from the catheter hub 18 when the needle is inserted in the bore 26 past or proximate the notch clip end 32, will selectively force the notch clip end 32 into contact with the side of the needle and thereby prevent the notch clip from disengaging the notch and thus lock the catheter hub and needle cover together. Stated yet analogously, as long as the catheter hub is fully engaged with the needle cover (e.g., FIGS. 4, 6–8) the non-forceful contact relationship or annular space 31 is maintained between the notch clip and the needle 12. However, the space 31 or non-forceful contact relationship is only selectively maintained therebetween if a user tries to disengage the catheter hub from the needle cover prematurely, e.g., when the needle is still in the second axial bore and protruding past or proximate the distal portion 32 of the notch clip.

Figure 14:
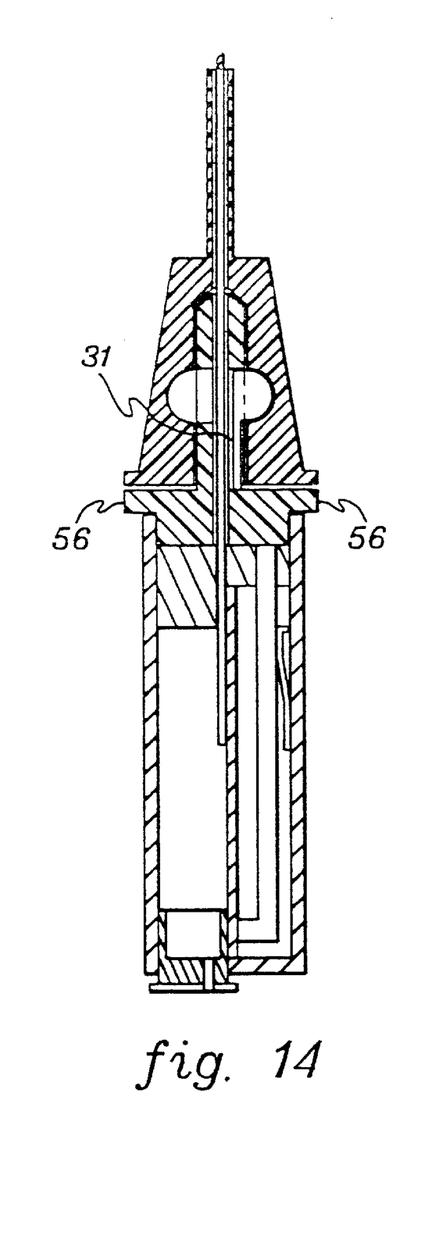
FIG. 14 is a cross-sectional side view of yet another embodiment of a safety intravenous catheter assembly in accordance with the features of the invention and similar in all respects to the assembly of FIG. 2, except here including an optional needle cover finger rest.

As understood herein, withdrawn, withdrawal or withdrawing means any movement of one member away from another member in the range from partial withdrawal (at least some portion of the respective members are still in communication with each other) to complete withdrawal (no portion of the respective members are in communication with each other). In this regard, when advancing catheter cannula 19 into a vessel and withdrawing the needle from catheter hub 18 which is still fully engaged with the needle cover 22 (FIGS. 7, 8), preferably the needle cover has a needle cover finger rest 56 (FIG. 14). Then, as the catheter cannula is advanced into a vessel and the needle is withdrawn from the second axial bore (FIG. 8, but without the finger rest 56 shown), the user can, if desired, hold or engage the exposed needle cover portion adjacent the stop bar 42, i.e., at the optional finger rest 56. In this way, one can advance the catheter cannula and withdraw the needle without pushing directly with the catheter hub by instead pushing the catheter hub via the needle cover 22 and most preferably the finger rest 56, thereby enabling cannula advancement and withdrawal of the needle with minimal, and preferably no, friction between the needle and the notch clip. The finger rest 56 may comprise an annular ring or one or more protrusions extending from the needle cover. Also, it is preferred that the finger rest 56 extend no further than the outer circumference of the adjacent portion of the catheter hub 18, though a longer extension may be desired by some users. Alternatively, instead of using finger rest 56, the user can advance the cannula and withdraw the needle by pushing directly with catheter hub 18.

Turning to the next step, just before the needle tip 16 is located prior to distal portion 32 of the notch clip, preferably the stop bar 42 is prevented from moving back into the needle case by detent 47 (FIG. 8). Then, once the needle is withdrawn enough so that the notch clip releases the catheter hub (i.e., needle tip 16 is located prior to the distal portion 32 of the notch clip) the notch clip can be forced into the second axial bore as the catheter hub begins disengagement from the needle cover (FIG. 9). At this time the end of the stop bar 42 abuts the inside distal end of the needle case 44, and then the user separates the needle case 44, needle 12 and needle cover 22 combined, from the catheter hub 18 (FIG. 10).

The step of forcing the notch clip 30 into the second axial bore 26 preferably begins as the step of disengaging the catheter hub begins. The notch clip flexibility, material characteristics and shape are such that the catheter hub can be freely disengaged from the needle cover with minimal resistance from the notch clip. Further in this regard, depending on the size of the second axial bore and the distal portion 32 of the notch clip, a notch 54 may be made in the needle cover 22 opposite the notch clip distal portion (e.g., FIGS. 2–12, 14). In this way, the notch clip distal portion can be assured positioning completely out of engagement with the notch during withdrawal of the needle cover from the catheter hub. However, when the needle diameter is sufficiently large, a notch 54 is not needed if the second axial bore will be large enough to ensure the notch clip distal portion completely disengages the notch during withdrawal of the needle cover from the catheter hub FIG. 13).

Various additional uses can be made with the assembly 10. For example, referring to FIG. 5, to assist in the insertion of the cannula into a blood vessel or body cavity, a flexible guide wire (not shown) can be inserted via an opening 52 in the chamber 43a and advanced into the first end 46 of the needle and made to exit the tip 16 (i.e., Seldinger wire technique for vascular access). In this regard a minor modification (not shown) of chamber 43's internal shape would facilitate easy access of a flexible guide wire into needle end 46. Alternatively, a syringe (not shown) can be attached to the chamber 43a via the opening 52, for communicating a fluid to or from the chamber 43a. Although not shown, opening 52 may be located in the center of the proximal end of the needle case, which is accomplished by making conventional modifications of the needle case.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A safety intravenous catheter assembly, comprising:
    a needle comprising a tip and an opposite end;
    a catheter hub;
    a needle cover attachable to and releaseably lockable with said catheter hub when said needle extends through said needle cover;
    a stop assembly comprising a needle case attached to said opposite end of said needle, a stop bar having an end attached to said needle cover, and a spring-biased detent; and
    wherein after use of said safety intravenous catheter assembly, an opposite end of said stop bar is engagable with said detent to form a first locking position wherein said tip is locked in said needle cover and said catheter hub cannot disengage from said needle cover, and after said needle tip is locked within said needle cover, said stop bar being movable to a second locking position wherein said catheter hub can disengage from said needle cover.

2. The assembly of claim 1 wherein said needle cover includes a finger rest.

3. The assembly of claim 1 wherein said catheter hub is rotatable relative to said needle cover.

4. The assembly of claim 1 wherein said needle cover is receivable within said catheter hub.

5. A method for using a safety intravenous catheter assembly, the method comprising:
    obtaining a safety intravenous catheter assembly of claim 1 having a catheter hub releaseably locked to a needle cover with a needle extending through the needle cover and a tip of the needle extending from the catheter hub;
    withdrawing the tip of the needle into the needle cover;
    locking the tip of the needle within the needle cover; and
    allowing detachment of the catheter hub from the needle cover only after the needle tip is locked within the needle cover.

6. The method of claim 5 further comprising rotating the catheter hub relative to the needle cover when the catheter hub is releaseably locked to the needle cover.

7. The method of claim 5 further comprising a catheter cannula attached to the catheter hub and wherein the tip of the needle extends through the catheter cannula when the catheter hub is releaseably locked to the needle cover, and further comprising inserting the catheter cannula and needle tip into a patient.

8. The method of claim 5 wherein the needle cover includes a finger rest.

9. The method of claim 8 wherein the finger rest has an outer circumference portion at least as great as an outer circumference portion of the catheter hub.

10. A safety intravenous catheter assembly for use with a needle, comprising:
    a catheter hub having a first axial bore extending through the catheter hub;
    a needle cover having a first end of the needle cover insertable in the first axial bore and a second axial bore extending through the needle cover and co-axial with the first axial bore;
    a notch extending outwardly in the first axial bore of the catheter hub;
    a notch clip positionable to engage the notch of the catheter hub and lock the catheter hub in engagement with the needle cover when the needle cover is inserted in the first axial bore and a tip of the needle is inserted in the second axial bore at least adjacent or past a distal portion of the notch clip, wherein the notch clip disengages the notch and enables the catheter hub to pass out of engagement with the needle cover when the tip of the needle is located in the second axial bore prior to the distal portion of the notch clip, wherein the notch clip is maintainable adjacent the needle throughout a range of positions from being in forceful contact with the needle to being spaced from the needle when the needle cover is inserted in the first axial bore and the tip of the needle is inserted in the second axial bore at least adjacent or past the distal portion of the notch clip, wherein the notch clip is maintainable adjacent the catheter hub throughout a range of positions from being in forceful contact with the catheter hub to being spaced from the catheter hub when the needle cover is inserted in the first axial bore and the tip of the needle is inserted in the second axial bore at least adjacent or past the distal portion of the notch clip, wherein the notch clip does not intersect the second axial bore when the notch clip is in a non-biased position and wherein the notch clip and the needle are in a frictionless to near frictionless relationship relative to one another when the notch clip is in the non-biased position and the needle is moved relative to the notch clip.

11. A method for using a safety intravenous catheter assembly in combination with a needle, the safety intravenous catheter assembly including a catheter hub having a first axial bore extending therethrough, the method comprising:
    withdrawing the needle from a second axial bore, the second axial bore being located in a needle cover and the needle cover including a notch clip positionable in engagement with an outward extending notch in a catheter hub;
    selectively maintaining the notch clip throughout a range of positions from being in forceful contact with the needle to being spaced from the needle when the needle cover is inserted in the first axial bore and a tip of the needle is inserted in the second axial bore at least adjacent or past a distal portion of the notch clip;

selectively maintaining the notch clip throughout a range of positions from being in forceful contact with the catheter hub to being spaced from the catheter hub when the needle cover is inserted in the first axial bore and the tip of the needle is inserted in the second axial bore at least adjacent or past the distal portion of the notch clip;

selectively maintaining the notch clip in a non-intersecting relationship with the second axial bore when the notch clip is in a non-biased position;

sliding the needle relative to the notch clip in a frictionless to near frictionless relationship when withdrawing the needle from the second axial bore;

forcing the notch clip into the second axial bore; and disengaging the catheter hub from the needle cover.

12. A safety intravenous catheter assembly, comprising:

a needle comprising a tip and an opposite end;

a catheter hub;

a needle cover attachable to and releaseably lockable with said catheter hub when said needle extends through said needle cover;

a stop assembly comprising a needle case attached to said opposite end of said needle, a stop bar having an end attached to said needle cover and an opposite end disposed in said needle case, and a spring-biased detent attached to said needle case;

wherein after use of said safety intravenous catheter assembly, said opposite end of said stop bar is engagable with said detent to form a first locking position wherein said tip is locked in said needle cover and said catheter hub cannot disengage from said needle cover, and after said needle tip is locked within said needle cover, said stop bar is movable to a second locking position wherein said catheter hub can disengage from said needle cover.

13. The assembly of claim 12 wherein said needle cover includes a finger rest.

14. The assembly of claim 12 wherein said catheter hub is rotatable relative to said needle cover.

15. The assembly of claim 12 wherein said needle cover is receivable within said catheter hub.

16. A method for using a safety intravenous catheter assembly, the method comprising:

obtaining a safety intravenous catheter assembly of claim 12 having a catheter hub releaseably locked to a needle cover with a needle extending through the needle cover and a tip of the needle extending from the catheter hub;

withdrawing the tip of the needle into the needle cover;

locking the tip of the needle within the needle cover; and allowing detachment of the catheter hub from the needle cover only after the needle tip is locked within the needle cover.

17. The method of claim 16 further comprising rotating the catheter hub relative to the needle cover when the catheter hub is releaseably locked to the needle cover.

18. The method of claim 16 further comprising a catheter cannula attached to the catheter hub and wherein the tip of the needle extends through the catheter cannula when the catheter hub is releaseably locked to the needle cover, and further comprising inserting the catheter cannula and needle tip into a patient.

19. The method of claim 16 wherein the needle cover includes a finger rest.

20. The method of claim 19 wherein the finger rest has an outer circumference portion at least as great as an outer circumference portion of the catheter hub.

21. A safety intravenous catheter assembly, comprising:

a needle comprising a tip and an opposite end;

a catheter hub;

a needle cover attachable to and releaseably lockable with said catheter hub when said needle extends through said needle cover;

a stop assembly attached to said opposite end of said needle to said needle cover, said stop assembly comprising, after use of said safety intravenous catheter assembly, a first locking position wherein said tip is irreversibly locked in said needle cover and said catheter hub cannot disengage from said needle cover, and after said needle tip is irreversibly locked within said needle cover, a second locking position wherein said catheter hub can disengage from said needle cover; and wherein said stop assembly comprises a ring-like stop and said needle has a stop notch located in a side of said needle, and said stop notch defining said first and second irreversible locking positions.

22. The assembly of claim 21 wherein said ring-like stop comprises a resilient material.

* * * * *